United States Patent
Rose et al.

(10) Patent No.: US 12,226,243 B2
(45) Date of Patent: Feb. 18, 2025

(54) COMPUTER-ASSISTED TOMOGRAPHY SYSTEM

(71) Applicant: OTTO-VON-GUERICKE-UNIVERSITÄT MAGDEBURG, Magdeburg (DE)

(72) Inventors: Georg Rose, Magdeburg (DE); Thomas Hoffman, Magdeburg (DE); Mathias Leopold, Magdeburg (DE); Oliver Großer, Magdeburg (DE); Maciej Pech, Magdeburg (DE)

(73) Assignee: OTTO-VON-GUERICKE-UNIVERSITÄT MAGDEBURG, Madgeburg (DE)

( * ) Notice: Subject to any disclaimer, the term of this patent is extended or adjusted under 35 U.S.C. 154(b) by 277 days.

(21) Appl. No.: 17/787,630

(22) PCT Filed: Dec. 16, 2020

(86) PCT No.: PCT/EP2020/086516
§ 371 (c)(1),
(2) Date: Aug. 14, 2022

(87) PCT Pub. No.: WO2021/130084
PCT Pub. Date: Jul. 1, 2021

(65) Prior Publication Data
US 2022/0409148 A1 Dec. 29, 2022

(30) Foreign Application Priority Data
Dec. 23, 2019 (DE) .................... 10 2019 135 782.9

(51) Int. Cl.
*A61B 6/03* (2006.01)
*A61B 6/04* (2006.01)
(Continued)

(52) U.S. Cl.
CPC ............ *A61B 6/035* (2013.01); *A61B 6/0407* (2013.01); *A61B 6/06* (2013.01); *A61B 6/12* (2013.01)

(58) Field of Classification Search
None
See application file for complete search history.

(56) References Cited

U.S. PATENT DOCUMENTS 6,298,117 B1 * 10/2001 Hampel .................. A61B 6/06
378/150
2009/0281452 A1 * 11/2009 Pfister .................. A61B 6/5229
600/567
(Continued)

FOREIGN PATENT DOCUMENTS

EP 0982002 A1 3/2000
JP 2011507581 A 3/2011
(Continued)

*Primary Examiner* — Marcus H Taningco
(74) *Attorney, Agent, or Firm* — WCF IP

(57) ABSTRACT

The invention relates to a computer-assisted tomography (CT) system having the following features: a) at least one X-ray source, b) at least one patient couch for supporting a patient, c) at least one collimator in the ray path of the X-rays from the X-ray source through the patient, wherein a targeted X-ray from among the total X-ray radiation of the X-ray source is radiated by the collimator onto the patient, d) at least one X-ray detector, provided permanently or at least temporarily in the ray path of the targeted X-ray radiated by the collimator through the patient, e) at least one automatically actuable drive mechanism, using which the collimator can be moved with respect to the radiation direction of the targeted X-ray passing through the collimator, relative to the patient and/or to the X-ray detector, f) at least one electronic control device that is configured to automatically actuate the drive mechanism.

10 Claims, 3 Drawing Sheets

Figure 1:
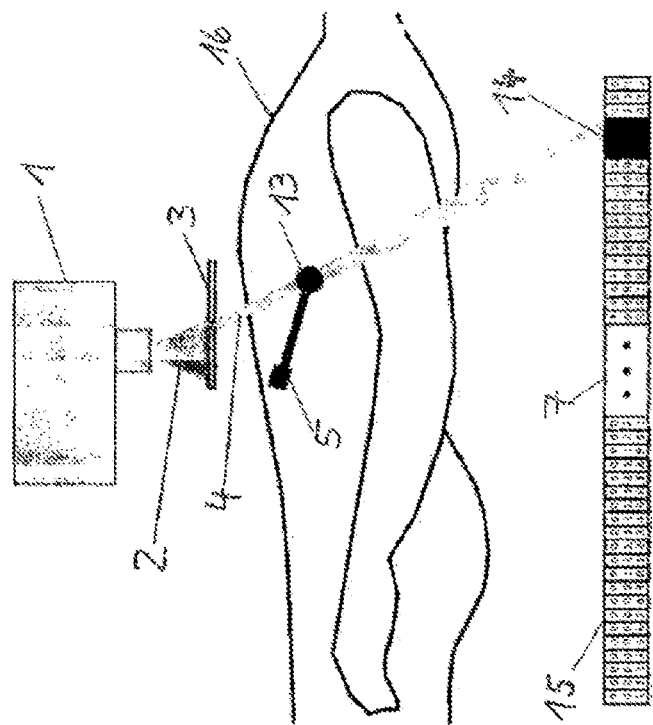

(51) Int. Cl.
 *A61B 6/06* (2006.01)
 *A61B 6/12* (2006.01)

(56) References Cited

U.S. PATENT DOCUMENTS

| | | | |
|---|---|---|---|
| 2010/0274120 A1 | 10/2010 | Heuscher | |
| 2012/0002780 A1* | 1/2012 | Forthmann | G16H 50/30 |
| | | | 382/128 |
| 2015/0297158 A1* | 10/2015 | Bothorel | A61B 6/4435 |
| | | | 378/20 |
| 2016/0007950 A1* | 1/2016 | Lim | A61B 6/548 |
| | | | 378/150 |
| 2021/0145373 A1* | 5/2021 | Biju | G01N 23/046 |
| 2021/0259648 A1* | 8/2021 | Jeanmaire | A61B 6/469 |

FOREIGN PATENT DOCUMENTS

| WO | 2009083851 A1 | 7/2009 |
|---|---|---|
| WO | 2009-141766 A2 | 11/2009 |

\* cited by examiner

COMPUTER-ASSISTED TOMOGRAPHY SYSTEM

The invention relates to a computed tomography system, also referred to below as a CT system, for computed tomographic examinations and treatments on patients.

A CT system is known, for example, from DE 10 2013 2019 676 A1. For certain CT recordings, the X-rays emitted by an X-ray tube of the CT system may, for example, be collimated by apertures.

The object of the invention is to further improve such a CT system in respect of functionality.

This object is achieved by a CT system having the following features:
 a) at least one X-ray source,
 b) at least one patient table for supporting a patient,
 c) at least one collimator in the beam path of the X-rays from the X-ray source through the patient, a directed X-ray beam selected from the entire X-radiation of the X-ray source being emitted to the patient through the collimator,
 d) at least one X-ray detector, which is arranged permanently or at least temporarily in the beam path of the directed X-ray beam from the collimator through the patient,
 e) at least one automatically actuatable drive mechanism by which the collimator can be adjusted in respect of the emission direction of the directed X-ray beam transmitted by the collimator relative to the patient and/or the X-ray detector,
 f) at least one electronic control device, which is adapted for automatic actuation of the drive mechanism.

The CT system according to the invention may in this way be improved by an active collimator. Such an active collimator makes it possible to assist examinations and treatments by means of the CT system by automatic assistance functions, for example automatic alignment of the directed X-ray beam by means of adjustment of the collimator to a desired position. Further assisting functions are also made possible, for example automatic tracking of instruments during interventions on the patient for dose reduction or volume-of-interest imaging, in which a patient's particular body region to be acquired, for example a particular organ, is purposely illuminated during and after rotation of the gantry by automatic alignment of the directed X-ray beam by means of adjustment of the collimator.

As may be gathered from the explanations above, the collimator is an apparatus with which a directed X-ray beam (also referred to as a working beam) having a particular solid angle is selected from the entire X-radiation emitted by the X-ray source and is transmitted to the patient. The collimator may for example be configured as an adjustable aperture, for example in the form of mutually displaceable plates with openings.

The X-ray detector may, for example, be configured as a multirow detector. A multirow detector combines the advantages of imaging with a high dynamic range (contrast resolution) as well as very accurate determination of the Hounsfield values and very short integration times. In addition or as an alternative, the X-ray detector may also be configured as a flat detector, which has the advantage of a very high spatial resolution and a large imaging region. The CT system may also comprise a plurality of such X-ray detectors, in which case one X-ray detector or the other may be used as required.

One important application field of the invention is the X-ray assisted image-guided intervention on a patient, for example needle placement for biopsy, instrument placement for tumor treatment, surgical operations and catheter-based interventions for the treatment of blood vessels. In this case, by means of the CT system according to the invention, the selection of the transmitted directed X-ray beam of the X-ray source may be combined with active automated layer and image detail tracking.

The electronic control device may, for example, comprise a computer which carries out particular control and/or regulation steps, for example by means of a computer program. The computer may be configured as a commercially available computer, for example as a PC, laptop, notebook, tablet or smartphone, or as a microprocessor, microcontroller or FPGA, or as a combination of such elements.

According to one advantageous configuration of the invention, the automatically actuatable drive mechanism is adapted to adjust the collimator in respect of the emission direction of the directed X-ray beam transmitted by the collimator relative to the patient and/or the X-ray detector in at least two spatial directions. The drive mechanism may, for example, be configured for two-dimensional adjustment of the collimator in the X and Z directions, for example with a mechanism similar to an industrial biaxial positioning system.

According to one advantageous configuration of the invention, the control device is adapted to determine the position of an object in the region of the patient table and, as a function of the position determined, to adjust the collimator by means of the drive mechanism in such a way that the detected object lies in the region of the directed X-ray beam transmitted by the collimator, in particular at the center of the directed X-ray beam. The object may, for example, be a part of a medical instrument, for example for tumor treatment or catheter-based intervention, or a biopsy needle. In particular, it may be the distal end of such an instrument. In this way, the automatic function by means of the control device ensures that the object, or the instrument, always lies in the imaging region of the CT system.

According to one advantageous configuration of the invention, the control device is adapted for automatic tracking of the detected object when the position of the object varies, and to track the collimator by means of the drive mechanism to the varying position in respect of the emission direction of the directed X-ray beam. This allows automatic tracking of the directed X-ray beam with the object, for example the medical instrument. In this way, the user is relieved even more from manual actions. The automatic function of the control device ensures that the object, or the instrument, still lies in the acquisition region of the CT imaging in the event of a position variation.

According to one advantageous configuration of the invention, the control device is adapted to determine the position of the object by means of image processing with the aid of the projections and reconstructed 3D datasets obtained by means of the X-ray detector. This has the advantage that no additional sensor elements are needed for the position acquisition, and if applicable the tracking of the object. The projections and reconstructed 3D datasets acquired by means of the CT image acquisition can be used directly. Depending on the type of X-ray detector used, for example, a 3D approach or a 2D approach may in this case be adopted, as will be explained in more detail below with the aid of examples. In particular, a multirow detector allows a 3D approach in the detection and tracking of an object in the CT images, that is to say three-dimensional coordinates of the object can be determined automatically from the CT images.

For the determination of the position of the object by means of image processing, it is possible to use an algorithm which detects the position and orientation from the projection images or reconstruction images of the instruments.

According to one advantageous configuration of the invention, the control device is adapted to determine the position of the object with the aid of data of an external measuring instrument, which acquires the position of the object. Position acquisition of the object may therefore be carried out either only by the external measuring instrument or additionally by the external measuring instrument, as a supplement to the CT imaging.

According to one advantageous configuration of the invention, the control device has access to a dataset which specifies a desired direction profile of the directed X-ray beam, the control device being adapted, by means of the dataset, to adjust the collimator by means of the drive mechanism in such a way that the directed X-ray beam has a direction profile that corresponds to the direction profile of the dataset. A direction profile is in this case intended to mean a beam direction of the directed X-ray beam which varies over time. In this way, a particular predetermined path along which the directed X-ray beam is intended to be moved may be specified by means of automatic control. In this case, it is possible to specify not only the direction profile but, depending on the embodiment, also the speed of the adjustment and in general the behavior of the variation in the direction of the directed X-ray beam as a function of time. For example, it may be specified that the directed X-ray beam stays for some time in certain directions before it is adjusted to another direction.

According to one advantageous configuration of the invention, the CT system comprises a further drive mechanism by which the position of the patient relative to the gantry of the CT system is automatically adjustable, the electronic control device being adapted for automatic actuation of the further drive mechanism. The range of adjustment of the collimator by means of the automatically actuatable drive mechanism is generally limited by the maximum projection area on the detector. Depending on the type of examination or intervention on the patient, it may be necessary for CT imaging to take place over a region larger than is allowed by the adjustability of the collimator. To this end, it is advantageous for the patient's position to be adjustable automatically by means of the further drive mechanism so that a desired position of the patient can be placed in the image acquisition region of the CT system. For example, the further drive mechanism may be adapted to adjust the patient table or at least a supporting region of the patient table relative to the gantry.

According to one advantageous configuration of the invention, the drive mechanism and/or the further drive mechanism is configured as an electromechanical, hydraulic or pneumatic drive mechanism or as a combination of such drive mechanisms. This allows simple and economical production of a reliable drive mechanism. The drive mechanism may, for example, comprise an electric motor for moving the collimator or a hydraulically or pneumatically deployed actuating cylinder or a combination of a plurality of such elements. The same applies for the further drive mechanism.

According to one advantageous configuration of the invention, the control device is additionally adapted to control the X-ray source and to evaluate the signals of the X-ray detector. In this way, all necessary data are available in the control device, both in respect of the signals of the X-ray detector and in respect of the current position of the directed X-ray beam from the collimator. In this way, additional information may be combined together, which leads to a simplification of the CT imaging and an increase in the quality of the imaging.

According to one advantageous configuration of the invention, the CT system comprises at least one display unit for displaying CT images obtained from the signals of the X-ray detector. The CT images generated by the image reconstruction of the computed tomography may therefore be represented on the display unit, for example a screen.

Figure 3:
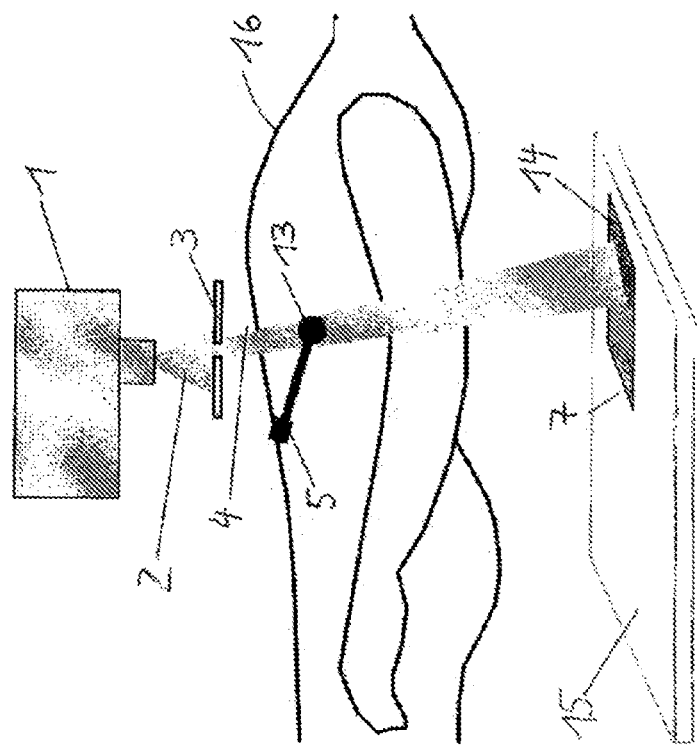
Figure 5:
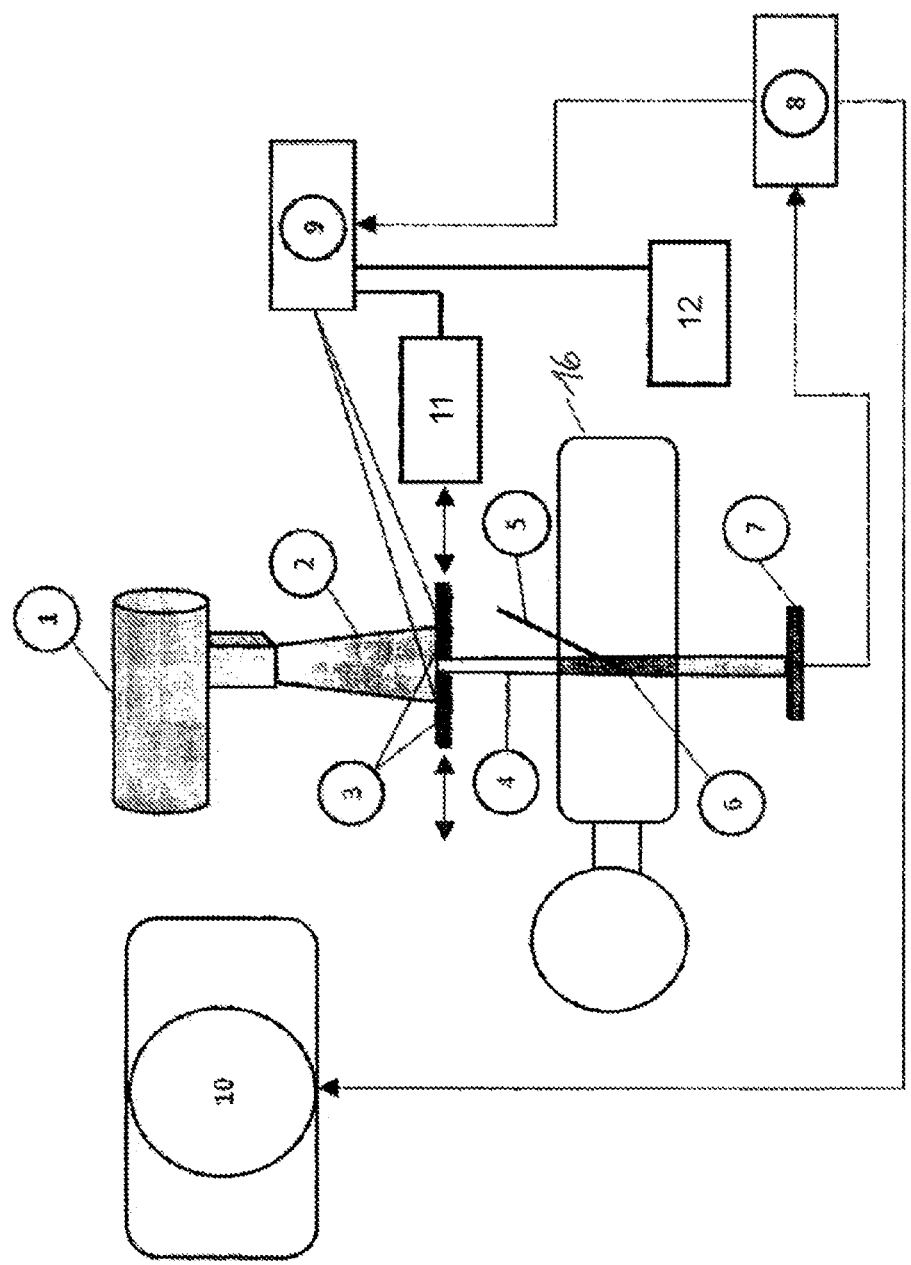

The invention will be explained in more detail below with the aid of exemplary embodiments with the use of drawings, in which:

FIG. 1, 2—shows a part of the CT system in a side view in the case of a multirow detector approach, and FIG. 3, 4—shows a part of the CT system in a side view in the case of a projection approach, and FIG. 5—shows a schematic block diagram of the overall CT system.

The CT system represented in the figures comprises an X-ray source 1, for example an X-ray tube, a collimator 3, an X-ray detector 7, an automatically actuatable drive mechanism 11 for adjusting the collimator 3, a further automatically actuatable drive mechanism 12, an electronic control device 8, 9, which may comprise a computer, and a display unit 10.

As may be seen in FIG. 1, a patient 16 lies on a patient table (not depicted) of the CT system. The X-ray source 1 emits X-rays in a beam path 2 to the collimator 3. Part of the X-radiation is shielded by the collimator 3 in such a way that only a directed X-ray beam 4 is transmitted by the collimator 3 to the patient 16. On the other side of the patient 3 from the X-ray source 1, or the collimator 3, there is the X-ray detector 7, for example the conventional multirow detector represented in FIGS. 1 and 2. By the automatically actuatable drive mechanism 9 (not represented in FIG. 1), the collimator 3 can be adjusted in such a way that the emission direction of the directed X-ray beam 4 is varied relative to the patient 16, or relative to the X-ray detector 7.

Figure 2:
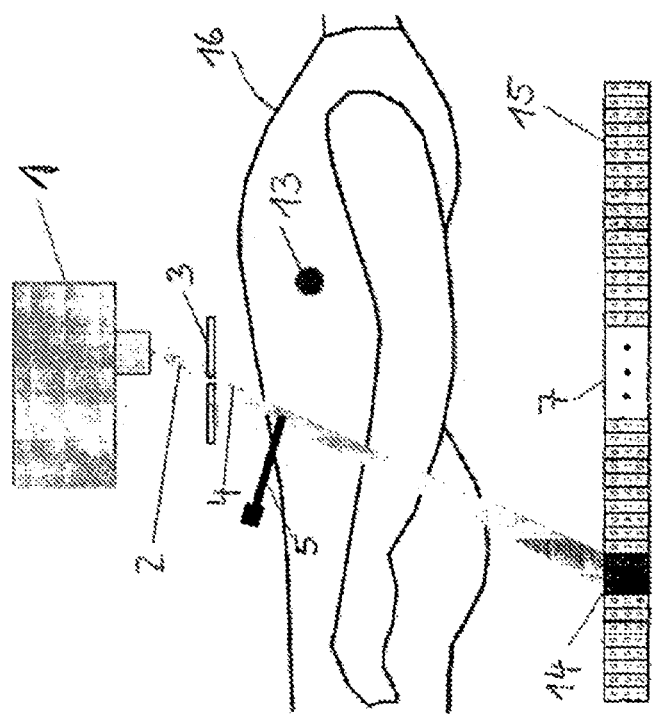

FIG. 1 shows a first region 14 of the X-ray detector 7, in this case lying relatively far to the left, which is irradiated by the directed X-ray beam 4. The other regions 15 of the X-ray detector 7 are not irradiated by the directed X-ray beam 4. If the collimator 3 is now adjusted as represented in FIG. 2, the direction of the directed X-ray beam 4 changes, for example, in such a way that the irradiated region 14 of the X-ray detector 7 now lies further to the right. The irradiated region 14 can be actively tracked.

In the examples of FIGS. 1 and 2, it is respectively assumed that an object 5, for example a medical instrument, is intended to be moved with image guidance from an arbitrary starting point, at which the object 5 is located in FIG. 1, to an end point 13 using automatic assistance by the CT system. This means that by the automatic control of the collimator 3 by means of the automatically actuatable drive mechanism 9 and the electronic control device 8, 9, the directed X-ray beam 4 is intended to be adjusted so that it always follows the position of the object 5, for example the distal end of the object 5. By this automatic tracking function, the object 5 is purposely tracked by continuous imaging of the distal end of the object 5 to the end point 13, which is reached in FIG. 2.

Figure 4:
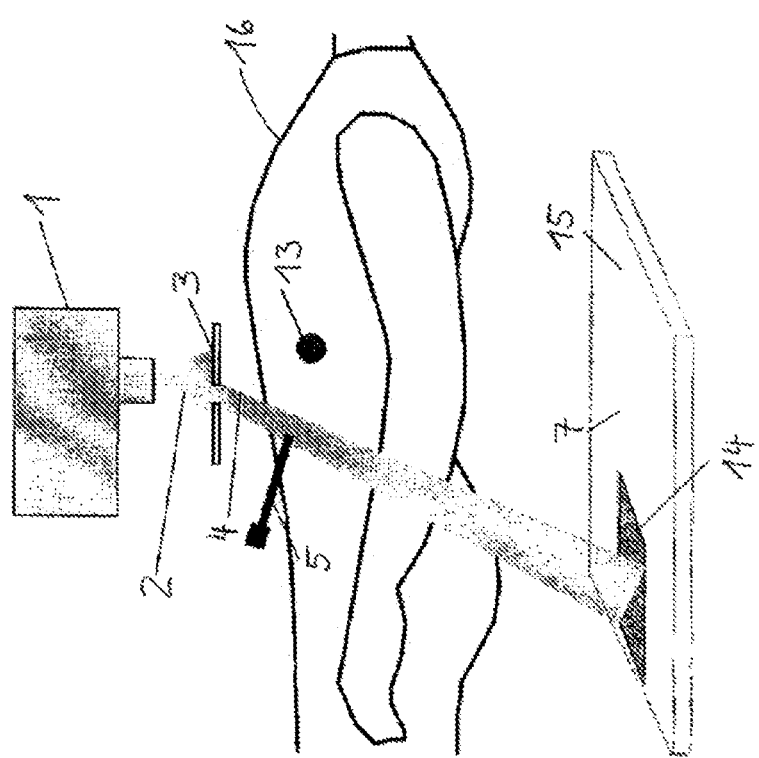

FIGS. 3 and 4 show a similar representation to FIGS. 1 and 2, as well as the same process of tracking the object 5 from a starting point to the end point 13. In contrast to FIGS. 1 and 2, in this case a different X-ray detector 7 is used, for example a flat detector. In contrast to FIGS. 1 and 2, in which a multirow detector approach may be carried out, a 2D approach of the instrument guiding may be carried out in FIGS. 3 and 4.

Multirow Detector Approach:

The aim is, in the scope of a (minimally invasive) image-guided intervention, to have the instrument required for the treatment or the organ to be observed constantly located in the image detail. The instrument is in this case guided freehand by the doctor or, for example, by means of a robot. To date, the centering of the patient has been performed by means of a manually controlled forward displacement of the patient table. The invention addresses, for example, the problem of needle imaging in a fluoroscopic 3D image by means of active layer tracking of the collimator 3 on the tube side. This approach offers the advantage that the intervention can be carried out without interruption and manual readjustment of the patient table is not necessary. In particular, automatic volume-of-interest imaging is possible, in which a patient's particular body region to be acquired, for example a particular organ, is purposely illuminated during and after rotation of the gantry by automatic alignment of the directed X-ray beam by means of adjustment of the collimator.

For fluoroscopic 3D imaging, only a few layers of the detector are used since simultaneous representation as a tomographic image would not otherwise be possible. In this case, however, it is unimportant which detector rows contribute to the interventional fluoroscopic imaging. The detector rows may be driven individually. By means of collimation of the working ray beam which is only a few layers wide, the beam can be displaced over the entire depth of the collimator by means of changing the coordinates of the tube collimator. In current systems, this may be up to 512 detector rows, which with an exemplary pixel size of 0.5 mm amounts to about 256 mm. This means that with perpendicular guiding of the needle with respect to the collimated layer, the needle can be acquired over as much as 256 mm without having to displace the patient table.

In order to make the image reconstruction possible, it is advantageous to know the needle path beforehand or acquire it during the imaging. As an alternative, it is possible to record an entire projection dataset needed for the image reconstruction completely by rotation with a constant collimator layer. This allows updating as a function of the gantry rotation speed, which for CT systems available on the market is from 0.5 Hz to 5 Hz. The tracking of the collimator may in this case be performed to coordinates from image processing methods or external tracking methods (for example optical, electromagnetic). In the case of layers to be tracked which exceed the maximum depth of the detector, stepwise automated tracking of the patient table or positioning of the gantry system is advantageous. The layer tracking may therefore be configured as a combination of an active collimator and positioning of the gantry and/or of the patient table.

2D Approach:

In contrast to the 3D approach, in the 2D approach radiographic projections of larger-area volumes are represented instead of individual patient layers. This type of imaging is employed, inter alia, for vascular interventions and tumor treatments. An advantage over the 3D approach is the large-area observation and overview. A disadvantage is that the depth information is not provided. In the context of 2D projection, the active collimator system is intended to be used in order to reduce the irradiated area in which an instrument (for example a catheter) is located, and therefore reduce the dose for the patient.

FIG. 5 schematically shows the overall CT system. Again shown is the X-ray source 1 with the beam path 2 of the X-rays, which is restricted by the collimator 3 to form the directed X-ray beam 4. The directed X-ray beam 4 passes through the patient 16 to the X-ray detector 7. In this case, the layers 6 are recorded as projection images and, optionally, subsequently reconstructed to form a 3D dataset. The X-ray detector 7 sends the acquired signals to a processing computer 8, which is for example adapted for the recording of data, the reconstruction and the image processing. The processing computer 8 forms a part of the electronic control device. The processing computer 8 is connected to a controller 9, which is adapted to drive the automatically actuatable drive mechanism 11.

The controller 9 receives control signals from the processing computer 8. The controller 9 controls the drive mechanism 11 according to these control signals, so that the collimator 3 is adjusted in the desired way. In addition, the controller 9 may actuate a further automatically actuatable drive mechanism 12, for example in order to adjust the position of the patient relative to the CT gantry. For example, the patient table may be adjusted by the drive mechanism 12.

The processing computer 8 is furthermore coupled to the display unit 10. The CT images determined by means of the processing computer 8 can in this way be represented on the display unit 10.

The invention claimed is:

1. A computed tomography (CT) system, comprising:
   a) at least one X-ray source,
   b) at least one patient table for supporting a patient,
   c) at least one collimator in a beam path of X-rays from the at least one X-ray source through the patient, wherein a directed X-ray beam selected from X-radiation of the at least one X-ray source is emitted to the patient through the at least one collimator,
   d) at least one X-ray detector arranged permanently or at least temporarily in the beam path of the directed X-ray beam from the at least one collimator through the patient,
   e) at least one automatically actuatable drive mechanism by which the at least one collimator is adjusted with respect to an emission direction of the directed X-ray beam transmitted by the at least one collimator relative to the patient and/or the at least one X-ray detector,
   f) at least one electronic control device adapted for automatic actuation of the at least one automatically actuatable drive mechanism,
      wherein the at least one electronic control device is adapted to determine a position of an object in a region of the at least one patient table, and, as a function of the position of the object determined, to adjust the at least one collimator by the at least one automatically actuatable drive mechanism such that the position of the object lies in a region of the directed X-ray beam transmitted by the at least one collimator,
      wherein the at least on electronic control device is adapted for automatic tracking when the position of the object varies, and to track when the at least one collimator is moved to a varying position in respect to an emission direction of the directed X-ray beam by the at least one automatically actuatable drive mechanism, and
      wherein in a case of layers to be tracked which exceed a maximum depth of the at least one X-ray detector a stepwise automated repositioning of the at least one patient table or a gantry system of the CT system is performed, such that a layer tracking is configured as a combination of an active collimator and positioning of the gantry system and/or of the at least one patient table.

2. The CT system as claimed in claim 1, wherein the at least one automatically actuatable drive mechanism is adapted to adjust the at least one collimator with respect to the emission direction of the directed X-ray beam transmitted by the at least one collimator relative to the patient and/or the at least one X-ray detector in at least two spatial directions.

3. The CT system as claimed in claim 1 wherein the at least one electronic control device is adapted to determine the position of the object by image processing with aid of projections and reconstructed 3D datasets obtained by the at least one X-ray detector.

4. The CT system as claimed in claim 1 wherein the at least one electronic control device is adapted to determine the position of the object with aid of data of an external measuring instrument which acquires the position of the object.

5. The CT system as claimed in claim 1 wherein the at least one electronic control device has access to a dataset which specifies a desired direction profile of the directed X-ray beam, wherein the at least one electronic control device is adapted, by means of the dataset which specifies the direction profile of the directed X-ray beam, to adjust the at least one collimator by the at least one automatically actuatable drive mechanism such that the directed X-ray beam has a direction profile that corresponds to a direction profile of the dataset which specifies the desired direction profile of the directed X-ray beam.

6. The CT system as claimed in claim 1 further comprising a gantry, wherein the at least one automatically actuatable drive mechanism comprises a further drive mechanism by which a position of the patient relative to the gantry of the CT system is automatically adjustable, and wherein the at least one electronic control device is adapted for automatic actuation of the further drive mechanism.

7. The CT system as claimed in claim 6 wherein the at least one automatically actuatable drive mechanism and/or the further drive mechanism is configured as an electromechanical, hydraulic or pneumatic drive mechanism or as a combination thereof.

8. The CT system as claimed in claim 1 wherein the at least one electronic control device is adapted to control the at least one X-ray source and to evaluate signals of the at least one X-ray detector.

9. The CT system as claimed in claim 1 further comprising at least one display unit for displaying CT images obtained from signals of the at least one X-ray detector.

10. The CT system as claimed in claim 1 wherein the region of the directed X-ray beam is a center of the directed X-ray beam.

* * * * *